(12) United States Patent
Zhang et al.

(10) Patent No.: US 11,297,864 B2
(45) Date of Patent: Apr. 12, 2022

(54) APPLE ENZYME FOR EFFICIENT RECONSTRUCTION OF INTESTINAL MICROECOLOGY AND PROCESSING TECHNOLOGY

(71) Applicant: SDIC ZHONGLU FRUIT JUICE CO., LTD., Beijing (CN)

(72) Inventors: Jiming Zhang, Beijing (CN); Chuanzhu Leng, Beijing (CN); Xihong Li, Beijing (CN); Gang Xin, Beijing (CN); Xinfei Song, Beijing (CN); Baoshuang Tian, Beijing (CN); Nan Jiang, Beijing (CN); Qingfei Cao, Beijing (CN); Rui Huang, Beijing (CN); Meijun Du, Beijing (CN); Qingshan Zhang, Beijing (CN); Xiangyang Zheng, Weihai (CN)

(*) Notice: Subject to any disclaimer, the term of this patent is extended or adjusted under 35 U.S.C. 154(b) by 95 days.

(21) Appl. No.: 17/072,855

(22) Filed: Oct. 16, 2020

(65) Prior Publication Data

US 2021/0120858 A1    Apr. 29, 2021

(51) Int. Cl.
| | |
|---|---|
| *A23L 29/00* | (2016.01) |
| *A23L 33/10* | (2016.01) |
| *A23L 33/21* | (2016.01) |
| *C12N 9/42* | (2006.01) |
| *C12N 9/24* | (2006.01) |
| *C12N 1/18* | (2006.01) |
| *C12N 1/20* | (2006.01) |
| *C12N 1/22* | (2006.01) |

(52) U.S. Cl.
CPC ............... *A23L 29/06* (2016.08); *A23L 33/10* (2016.08); *A23L 33/21* (2016.08); *C12N 9/2402* (2013.01); *C12N 9/2437* (2013.01); *C12N 1/18* (2013.01); *C12N 1/20* (2013.01); *C12N 1/22* (2013.01)

(58) Field of Classification Search
CPC ..... A23L 29/06; C12N 9/2402; C12N 9/2437; C12N 1/20; C12N 1/18; C12Y 302/01004
See application file for complete search history.

(56) References Cited

U.S. PATENT DOCUMENTS

| 8,957,201 B2 | 2/2015 | Kaneko et al. |
| 2020/0171074 A1 | 6/2020 | Yang et al. |
| 2020/0190552 A1 | 6/2020 | Ju |

FOREIGN PATENT DOCUMENTS

| CN | 109123628 A | 1/2019 |
| CN | 110403115 A | 11/2019 |

*Primary Examiner* — Iqbal H Chowdhury

(57) ABSTRACT

The present invention relates to an apple enzyme for efficient reconstruction of an intestinal microecology and a processing technology, which comprises the following steps: (1) pretreating raw materials; (2) pulping; (3) detoxifying patulin: firstly biologically detoxifying the pulp: inoculating inoculating plant *Lactobacillus* (ATCC 8014) into the pulp, adjusting the pH to 3-7 at the temperature of 20-30° C., stirring, and detoxifying for 20-24 h; and then repeatedly absorbing and filtering with a carboxylation nano multiwall carbon-neutral aluminum oxide filter screen for three times; and (4) carrying out the division intensified and dynamic fermentation. For the problems of the apple enzymes such as low fermentation efficiency and long time, the division decompression dynamic intensified fermentation method of substrates is used, so that the high-speed and high-efficient fermentation of the apple can be realized, and the fermentation time can be greatly shortened.

3 Claims, 1 Drawing Sheet

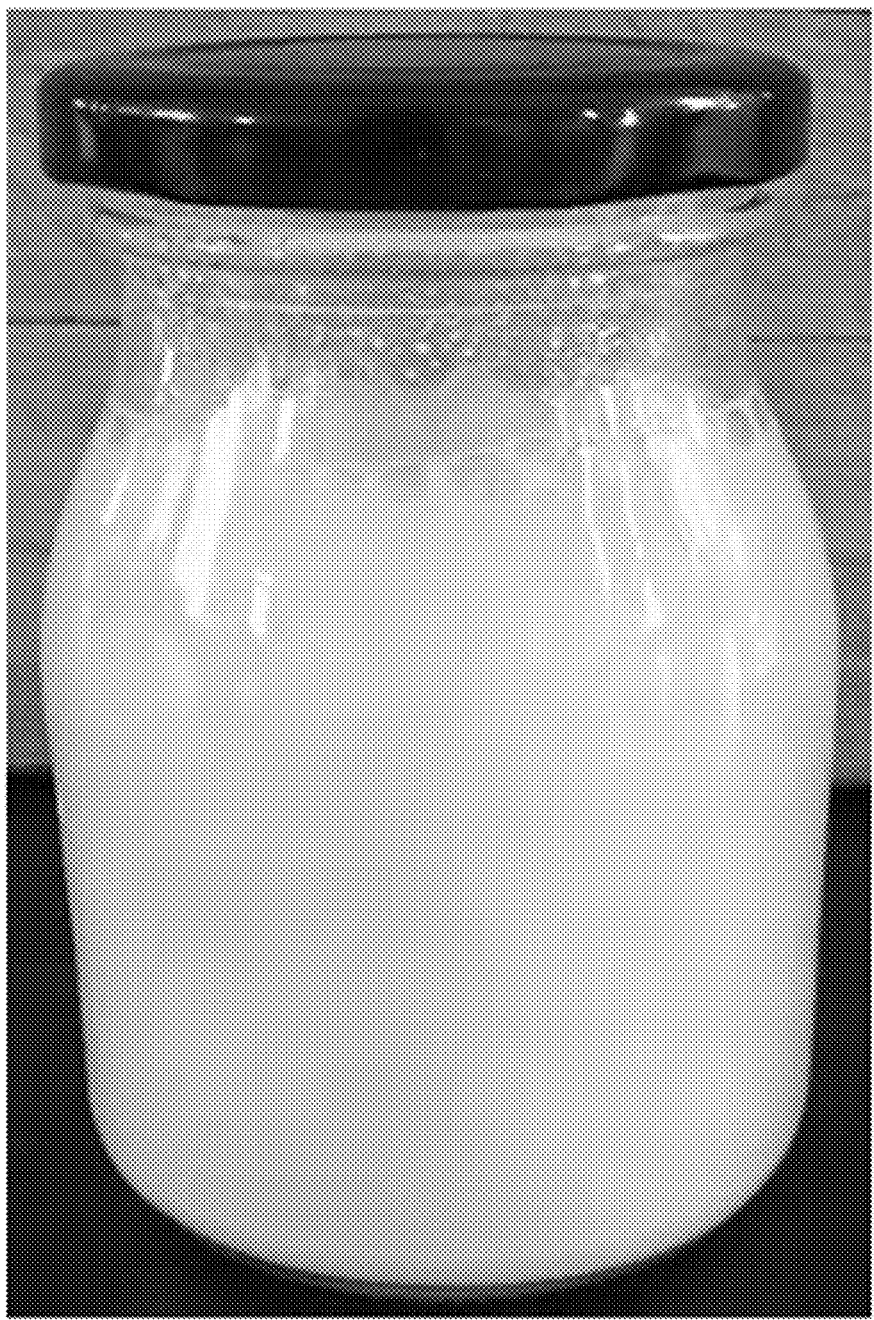

APPLE ENZYME FOR EFFICIENT RECONSTRUCTION OF INTESTINAL MICROECOLOGY AND PROCESSING TECHNOLOGY

CROSS-REFERENCE TO RELATED APPLICATIONS

This application claims priority to Chinese Patent Application No. 201911020617.9 with a filing date of Oct. 25, 2019. The content of the aforementioned applications, including any intervening amendments thereto, are incorporated herein by reference.

TECHNICAL FIELD

The present invention belongs to the field of enzymes, and relates to an apple enzyme for efficient reconstruction of intestinal microecology and a processing technology.

BACKGROUND OF THE PRESENT INVENTION

Enzymes are living enzymes and are prepared by fermenting food materials such as one or more fruits and vegetables through various natural probiotics adhering on the surface of the raw material and are fermented products rich in various enzymes, pectin, cellulose, mineral microorganisms, etc. The apple enzymes are rich in proteins, calcium, phosphorus, iron, zinc, potassium, magnesium, sulfur, carotene, vitamin B1, vitamin B2, vitamin C, niacin, cellulose and other nutrients. Research found that the apple is not only rich in nutrients that are necessary to the brain such as sugar, vitamins and minerals, but more importantly, are rich in zinc, which is conducive to promoting the growth and development and to improving the intelligence and memory.

At present, due to the reasons such as drugs, diet, ages, abnormal intestinal motility, immunity dysfunction and the like, most people in China are prone to intestinal microecological disorders. The long-term and large-scale use of broad-spectrum antibiotics is a main cause of the imbalance of intestinal flora in human bodies. Based on a health preservation concept, the apple enzymes as an optimum intestinal flora regulator are increasingly valued, and the nutritional concept is continuously popularized. With rich nutrients, the apple enzymes activate the cell viability and bring about certain benefit to the human body. Therefore, a lot of successful people caring about the health in China begin to drink the apple enzymes. Due to the simplicity in processing, the apple enzymes are generally hand-made in a small-scale homemade manner. The selection and treatment of raw materials and the control of fermentation conditions directly affect the quality of the apple enzymes, so that on the premise of increasing the utilization rate of the raw materials, to improve the fermentation efficiency, the flora abundance and the activity of relevant enzymes is the focus of the production and processing of the apple enzymes.

By searching, the following patent documents related to the present application are discovered. The specific disclosure is as follows:

1. "A method for simultaneously preparing apple brandy and apple pulp enzyme powder by using fresh apple pomace" (invention patent No.: ZL201510852062.X, authorization date: Jan. 12, 2018): the invention discloses a method for simultaneously preparing apple brandy and apple pulp enzyme powder by cold crushing and pulping the apple pomace after the solid fermentation, removing peels and seeds and transferring into a dryer for distillation and drying after the separation. The invention has the advantages that the apple enzyme for efficient reconstruction of intestinal microecology is prepared while the apple brandy is prepared, and the processing technology of the pulp enzyme powder is simple in operation. The disadvantages of the patent: (1) in the drying and renaturation process of the enzyme powder, the vitality of most probiotics and the activity of the enzymes may be reduced; (2) the enzyme powder prepared from the apple pomace is poor in taste, low in probiotics abundance and low in content of other nutrients; and (3) the traditional conventional technology is used to perform the solid fermentation for the pomace, while the enzyme fermentation time in the prior art is at least 3 to 6 months, so that the quality of the enzymes cannot be guaranteed.

2. "Composite fruit and vegetable enzymes and preparation method thereof" (invention patent No.: ZL201510617355.X, authorization date: Sep. 22, 2017): various fruits and vegetables are mixed and crushed and fermented by adding bacterial fluid and enzyme activity maintaining agent to prepare the composite fruit and vegetable enzymes. The invention has the advantages: the composite fruit and vegetable enzymes obtained by fermentation are complete in various enzymes and high in vitality. The disadvantages of the patent: (1) the composite fruits and vegetables are fermented collectively by *Aspergillus oryzae*, saccharomycetes and *Bacillus subtilis*, which are quite different in optimum fermentation conditions and have certain reciprocal inhibition effect, so that the fermentation efficiency and the bacterial strain abundance are relatively low; (2) by virtue of long-term standing fermentation, the deposition of raw materials and bacterial strains occurs, which is not conducive to the subsequent fermentation; and (3) the production period is relatively long, and the fermentation time is 500 to 1500 days.

3. "A preparation method of apple enzymes" (invention application No.: ZL201810979256.X, application date: Aug. 27, 2018): the raw material adopts core-removed sliced apples and is subjected to enzymolysis, yeast fermentation and acetic bacteria post fermentation to prepare the apple enzymes, which have the advantage that each bacterial strain can grow sufficiently according to the technological requirements, improves the fermentation efficiency and is high in nutritional value of fermentation metabolites. The disadvantages of the patent: (1) the core-removed apple slices are required as the raw material, so that the pretreatment requirement of the raw material is high, young fruits or defective fruits can be used, but there is the safety problem that patulin cannot be removed; (2) the applied bacterial strains are high in selection specificity for substrates and is poor in fermentation effect for the apple as the substrate; and (3) the activity of the enzymes and the abundance of the bacterial strain in a fermentation finished product are relatively low.

By summarizing the above patents, it is discovered that the existing apple enzyme processing technology has the following problems:

1. Low fermentation efficiency and long time: the fermentation time of the enzymes with low and medium quality by the traditional technology is about 1 to 3 months; the fermentation time of the high-quality enzymes is six months to more than one year, which is mainly because the specificity and an optimum growth condition regulation method of the applied bacterial strains as well as long-term standing fermentation and the deposition of the bacterial strains and the substrate are not conducive to the decomposition of the large-molecular substances, so that the fermentation efficiency is low.

2. Low probiotics abundance and low activity of relevant enzymes in the finished product are related to the quantity of the natural bacterial strains of the apple and the artificial bacterial strains participating in the fermentation; and additionally, a majority of probiotics and enzymes are extremely sensitive to the external unfavorable environment and are easy to die or inactivate.

3. The requirement on the raw material is high, and the use of young fruits and defective fruits for fermentation has the potential safety hazard of the patulin: in order to improve the product taste and safety, the core-removed apple slices are generally used as the raw material in the traditional technology, and the post-floral fallen fruits and artificially-thinned young fruits of the apple can also be fermented to obtain the enzymes with the same value by fermentation, but have the potential hazard of patulin.

4. Most apple enzymes are broad-spectrum preparations and are poor in specificity for intestinal microecological disorders caused by different factors: common causes and symptoms of the intestinal microecological disorders are as follows: for the microecological disorders caused by antibiotics, cocci substitute bacilli to become a dominant bacterial community; the high-fat diet is likely to cause the decrease of the number of intestinal *Lactobacillus* flora and bifidobacteria flora; the psychological stress and physical stress may also reduce the number of intestinal *Lactobacillus* flora and bifidobacteria flora; and the number of intestinal total anaerobe, lactobacilli and bifidobacteria of old people is reduced.

SUMMARY OF PRESENT INVENTION

The purpose of the present invention is to provide an apple enzyme processing technology for rapidly and efficiently reconstructing an intestinal microecology of the human body and to solve the technical difficulties during the processing such as low fermentation efficiency and long fermentation time of young fruits and defective fruits, high content of patulin and low probiotics abundance and enzyme activity, etc.

The technical solution for achieving the purpose of the present invention is as follows:

A processing method of an apple enzyme for efficient reconstruction of an intestinal microecology comprises the following steps:

(1) Pretreating Raw Materials removing molded parts of post-floral fallen fruits and artificially-thinned young fruits, washing ash and soil on the surfaces of the fruits, reserving original wild yeasts of pericarp, removing cores and dicing;

(2)

pulping with low-temperature liquid nitrogen, reducing browning of pulp compared to untreated pulp, and reserving the activity of a majority of enzymes;

controlling the low temperature at 5-10° C., wherein the dripping amount of the liquid nitrogen is 2%-3.5%; after the pulping, carrying out the enzymolysis by appropriately reducing the pressure, adding 50 mg/L-70 mg/L of pectinase and 85 mg/L-100 mg/L of cellulase, and stirring for 1-2 h at 40-45° C.;

(3) Detoxifying Patulin firstly biologically detoxifying the pulp: inoculating plant *Lactobacillus* (ATCC 8014) into the pulp, adjusting the pH to 3-7 at the temperature of 20-30° C., stirring, and detoxifying for 20-24 h; and then repeatedly absorbing and filtering with a carboxylated nano multiwall carbon-neutral aluminum oxide filter screen for three times;

(4) Carrying Out the Dynamic Fermentation adding is composed of trehalose, mannitol and cysteine in a weight ratio of (1-2):(1-1.5):(1-2); and then equally dividing the apple pulp into five portions for separate fermentation:fermenting with saccharomycetes, *Lactobacillus plantarum*, *Lactobacillus acidophilus*, probiotic *bacillus*, *Bifidobacterium* and *Clostridium butyricum*;

supplying oxygen to the enzyme solution fermented under an anaerobic condition for 1-2 hours every two days, and stopping the oxygen supply to the enzyme solution fermented under aerobic and facultative anaerobic conditions for 2-3 hours every two days; at the same time, carrying out the temperature-varied exercise at a rate of ±2-4° C. every day to improve the stress resistance of the flora and to improve the strength of probiotics; and maintaining appropriate low pressure in the entire fermentation process, introducing the nitrogen to disturb the fermentation broth for 0.5-1 h every day, then returning the pressure, and re-suspending sediments, thereby improving the fermentation efficiency;

(5) precisely intensifying and mixing the probiotics: mixing the six fermentation broths in the above steps for use;

(6) filtering: carrying out three-level filtration to remove suspended solids and undecomposed residues on the surface:

① fermenting with saccharomycetes:adding fruit *Saccharomyces cerevisiae* (ATCC 9080) into the fermentation broth, and fermenting for 12 days at 28-30° C.;

② fermenting with *Lactobacillus plantarum*: adding 1%-1.5% of albumen powder into the fermentation broth, and inoculating plant *Lactobacillus* (ATCC 8014), followed by anaerobic fermentation for one week at 36-40° C.;

③ fermenting with *Lactobacillus acidophilus*: adding 2-3% of lactose and 1-1.5% of fructo-oligose into the fermentation broth, and inoculating *Lactobacillus acidophilus* (AS 1.1854), followed by oxygen-free fermentation for one week at 37° C.;

④ fermenting with probiotic *bacillus*: adding 1%-1.5% of albumen powder and 2-2.5% of starch into the fermentation broth, and inoculating probiotic *bacillus* (CGMCC1.3358), followed by aerobic fermentation for one week at 37° C.;

⑥ fermenting with *Bifidobacterium*: adding 2-3% of oligosaccharide and 1-1.5% of fructo-oligose into the fermentation broth, and inoculating *Bifidobacterium* (ATCC 15700), followed by the anaerobic fermentation for one week at 37° C.;

⑦ fermenting with *Clostridium butyricum*: adding 1-1.5% of lactose into the fermentation broth, and inoculating *Clostridium butyricum* (ATCC 19398), followed by the anaerobic fermentation for one week at 37° C.;

(7) adding a flavoring agent, blending and stirring adding 3-4 wt % of sucrose, 1-3 wt % of honey, 1-2 wt % of brown sugar, and 1-1.5 wt % of dark brown sugar, and fully and uniformly stirring;

(8) chelating and aging in a dark place sealing the blended apple enzymes, standing in a dark place, chelating and aging for 1 to more than 6 months, aging for one month to obtain the low-quality and medium-quality apple enzymes, and aging for more than six months to obtain the high-quality apple enzymes;

(9) exhausting the air regularly: opening a cover for air exhaustion every 15 days during the later aging period; and

(10) filtering: filtering again before obtaining the finished product.

Furthermore, a method for precisely intensifying and mixing the probiotics in step (5) comprises the following steps:

Precisely intensifying and mixing the probiotics for different target groups; mixing the saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth in a ratio of 1:1:1:1:1:1 for general population, in a ratio of 1:2:2:2:2:1 for people having intestinal microecological disorders caused by antibiotics, in a ratio of 1:1:2:1:2:1 for people having intestinal microecological disorders caused by high-fat diet, in a ratio of 1:1:2:1:2:1 for people having the intestinal microecological disorders caused by the psychological stress and physical stress and in a ratio of 1:2:2:1:2:2 for people having the intestinal microecological disorders caused by advanced ages.

Furthermore, a structure of the carboxylated nano multiwall carbon-neutral aluminum oxide filter screen is that the filter screen has a five-layer structure, wherein a first layer is a sieve plate with an aperture of 5-10 meshes (the diameter is about 2-4 mm); a second layer is carboxylated nano multiwall carbon with a particle size of 3-5 nm; a third layer is macroporous adsorption resin; a fourth layer is neutral aluminum oxide with a particle size of 50-70 μm; a fifth layer is also a sieve plate with an aperture of 5-10 meshes; and the pulp containing solute with a particle size not greater than 3 mm can pass through the adsorption filter screen.

Furthermore, a fermentation process using the saccharomycetes, *Lactobacillus plantarum*, *Lactobacillus acidophilus*, probiotic *bacillus*, *Bifidobacterium* and *Clostridium butyricum* comprises the following steps:

① Fermenting with saccharomycetes: adding fruit *Saccharomyces cerevisiae* (ATCC 9080) into the fermentation broth, and fermenting for 12 days at 28-30° C.;

② Fermenting with *Lactobacillus plantarum*: adding 1%-1.5% of albumen powder into the fermentation broth, and inoculating plant *Lactobacillus* (ATCC 8014), followed by anaerobic fermentation for one week at 36-40° C.;

③ Fermenting with *Lactobacillus acidophilus*: adding 2-3% of lactose and 1-1.5% of fructo-oligose into the fermentation broth, and inoculating *Lactobacillus acidophilus* (AS 1.1854), followed by oxygen-free fermentation for one week at 37° C.;

④ Fermenting with probiotic *bacillus*: adding 1%-1.5% of albumen powder and 2-2.5% of starch into the fermentation broth, and inoculating probiotic *bacillus* (CGMCC1.3358), followed by the aerobic fermentation for one week at 37° C.;

⑤ Fermenting with *Bifidobacterium*: adding 2-3% of oligosaccharide and 1-1.5% of fructo-oligose into the fermentation broth, and inoculating *Bifidobacterium* (ATCC 15700), followed by the anaerobic fermentation for one week at 37° C.;

⑥ Fermenting with *Clostridium butyricum*: adding 1-1.5% of lactose into the fermentation broth, and inoculating *Clostridium butyricum* (ATCC 19398), followed by the anaerobic fermentation for one week at 37° C.

The present invention has the advantages and beneficial effects:

1. In the present invention, the substrate is subjected to the division decompression dynamic intensified fermentation. First, pectinase and cellulase are added into the substrate to perform the constant-temperature decompression enzymolysis. Then the enzymolysis substrate is divided into multiple portions, and probiotics such as *Aspergillus oryzae*, *Lactobacillus*, *Bifidobacterium*, saccharomycetes and the like are added respectively into the portions to perform the separate decompression fermentation under the optimum conditions. During the fermentation process, the nitrogen is regularly introduced for a short time to disturb the fermentation broth so as to exchange upper and lower layers of fermentation broth, and then the pressure is returned. Finally, the fermentation products are mixed and blended. The optimum target substrates corresponding to the bacterial strains are added into the fermentation broths in the fermentation process, for example, starch and proteins are added into the *Aspergillus oryzae* fermentation broth, lactose is added into the *Lactobacillus* fermentation broth, and oligosaccharides such as fructose and galactose are added into the *Bifidobacterium* fermentation broth. The decompression purpose is to improve the inter-solute contact diffusion and permeation rate, to improve the fermentation efficiency and to shorten the fermentation time.

2. In order to reduce the use standard of the raw materials and increase the utilization rate of the raw materials, the present invention uses the post-floral fallen fruits and artificially-thinned young fruits of the apples to process the apple enzymes. The pulp of the apple is biologically degraded by plant *Lactobacillus*. A degradation product is repeatedly filtered and absorbed by the carboxylated nano multiwall carbon and neutral aluminum oxide filter screen for multiple times, thereby efficiently removing the patulin in the pulp, and eliminating the safety potential hazard.

3. In the present invention, according to the symptoms of different intestinal microecological disorders, the number of the corresponding bacterial strains is intensified. For the intestinal microecological disorders caused by antibiotics, the number of probiotic *bacillus*, *Lactobacillus* and bifidobacteria is intensified. For the microecological disorders caused by the high-fat diet and psychological stress as well as physical stress, the number of *Lactobacillus* and *Bifidobacterium* is intensified. For the gastrointestinal microecological disorders of the old people, the number of *Clostridium butyricum*, *Lactobacillus acidophilus* and *Bifidobacterium* is intensified. By specifically intensifying the number of different probiotic flora, the apple enzymes are more suitable for different people to eat, thereby implementing the efficient reconstruction of the intestinal microecology.

4. According to the present invention, the bacterial strains are subjected to the intermittent temperature change and oxygen supply and oxygen-deficient exercise to improve the adversity stress resistance of the probiotics. At the same time, the agent is added to maintain the vitality of the generated enzymes and original enzymes in the fermentation broth. The intermittent temperature change is mainly to regularly change the optimum fermentation culture temperature for a short time in the fermentation process, so that the bacterial strains can continuously break through the upper limit and lower limit of the adaptive temperature. At the same time, the anaerobic probiotics are subjected to the intermittent oxygen supply exercise; the aerobic and intermittent anaerobic probiotics are subjected to the oxygen-deficient exercise, so as to improve the strength of the bacterial strains, and improve the probiotics abundance of the finished product. By adding the agent, the high activity of relevant enzymes can be further maintained.

5. For the problems of the apple enzymes such as low fermentation efficiency and long time, the division decompression dynamic intensified fermentation method of the substrate is used, so that the high-speed and high-efficient fermentation of the apple can be realized, and the fermentation time can be greatly shortened. After the raw materials are pulped, the substrate is subjected to the decompression enzymolysis and fermentation and is divided into multiple portions, and the probiotics are added into the portions for separate fermentation under the optimum condition. At the same time, the optimum substrates such as the starch, proteins, lactose and the like are added into the fermentation broths, and the nitrogen is regularly introduced for a short time to disturb the fermentation broth, and the fermentation environment is appropriately kept at the low pressure to accelerate the inter-solute diffusion and permeation rate, thereby implementing the dynamic intensified fermentation. Finally, the separate fermentation broths are blended and mixed to rapidly obtain the high-quality apple enzymes.

6. For the problem that the enzyme finished product is low in probiotics abundance and activity of relevant enzymes, besides the addition of varieties of the fermentation probiotics, the intermittent temperature change and oxygen supply and oxygen-deficient exercise method is used to improve the adversity stress resistance of the probiotics and to increase the survival rate. At the same time, by adding the agent, the high activity of the probiotics-generating enzymes and original enzymes can be improved and maintained.

7. For the safety potential hazard of the presence of patulin caused by using the young fruits and the defective fruits, the pulp is biologically detoxified by plant *Lactobacillus* and repeatedly filtered and absorbed for multiple times by the carboxylated nano multiwall carbon and neutral aluminum oxide filter screen, so that the patulin can be efficiently removed, and the toxin residue is far less than the health standard (GB14974-1994) for limited quantity of the patulin in apple and hawthorn products in China.

8. Symptoms and treatment methods of the intestinal microecological disorders caused by different factors are different. The apple enzymes are broad-spectrum preparations and do not have the specificity. For this problem, the method for precisely intensifying the probiotics for the target groups is used, so that the efficient reconstruction of the intestinal microecological disorders caused by the antibiotics, high-fat diet, psychological pressure and physiological stress, and advanced ages and the like can be realized.

DESCRIPTION OF THE DRAWINGS

FIG. 1 shows an apple enzyme fermentation broth.

DETAILED DESCRIPTION OF PREFERRED EMBODIMENTS

The present invention is further described below through specific embodiments. The following embodiments are only descriptive rather than limiting, and shall not be used to limit the protection scope of the present invention.

Apple enzymes for efficient reconstruction of an intestinal microecology and a processing technology, includes the following steps:

(1) Pretreatment of Raw Materials.

Molded parts of post-floral fallen fruits and artificially-thinned young fruits are removed, ash and soil on the surfaces of the fruits are washed, original wild yeasts of pericarp are reserved, and the fruits are diced after cores are removed.

(2) Pulping;

pulping is carried out with low-temperature liquid nitrogen, so that the browning of the pulp is reduced, and the activity of a majority of enzymes can be maintained. The low temperature is controlled at 5-10° C., and the dripping amount of the liquid nitrogen is 2%-3.5%. After the pulping, the enzymolysis is carried out by appropriately reducing the pressure, and 50 mg/L-70 mg/L of pectinase and 85 mg/L-100 mg/L of cellulase are added, followed by stirring for 1-2 h at 40-45° C.;

(3) Detoxification of Patulin

Firstly the pulp is biologically detoxified: plant *Lactobacillus* (ATCC 8014) is inoculated into the pulp, followed by stirring and detoxification for 20-24 h under the conditions that the temperature is 20-30° C., and the PH is 3-7. Then a carboxylated nano multiwall carbon-neutral aluminum oxide filter screen is used for repeated adsorption and filtration for three times. The detoxification effect (the detoxification residue is detected) is shown as table 1.

The structure of the adsorption filter screen is as follows: the filter screen has a five-layer structure, wherein a first layer is a sieve plate with an aperture of 5-10 meshes (the diameter of about 2-4 mm); a second layer is carboxylated nano multiwall carbon with a particle size of 3-5 nm; a third layer is macroporous adsorption resin; a fourth layer is neutral aluminum oxide with a particle size of 50-70 μm; and a fifth layer is also a sieve plate with an aperture of 5-10 meshes. The pulp containing solute with a particle size not greater than 3 mm can pass through the adsorption filter screen.

(4) Dynamic Fermentation

A agent is added into the detoxified apple pulp, wherein the agent is composed of trehalose, mannitol and cysteine in a weight ratio of (1-2):(1-1.5):(1-2). The apple pulp is equally divided into five portions which are subjected to separate intensified fermentation.

① Fermentation with saccharomycetes: fruit *Saccharomyces cerevisiae* (ATCC 9080) is added into the fermentation broth, followed by fermentation for 12 days at 28-30° C.;

② Fermentation with *Lactobacillus plantarum:* 1%-1.5% of albumen powder is added into the fermentation broth, and plant *Lactobacillus* (ATCC 8014) is inoculated, followed by temperature-preservation anaerobic fermentation for one week at 36-40° C.;

③ Fermentation with *Lactobacillus acidophilus:* 2-3% of lactose and 1-1.5% of fructo-oligose are added into the fermentation broth, and *Lactobacillus acidophilus* (AS 1.1854) is inoculated, followed by oxygen-free fermentation for one week at 37° C.;

④ Fermentation with probiotic *bacillus:* 1%-1.5% of albumen powder and 2-2.5% of starch is added into the fermentation broth, and probiotic *bacillus* (CGMCC1.3358) is inoculated, followed by aerobic fermentation for one week at 37° C.;

⑤ Fermentation with *Bifidobacterium:* 2-3% of oligosaccharide and 1-1.5% of fructo-oligose are added into the fermentation broth, and *Bifidobacterium* (ATCC 15700) is inoculated, followed by the anaerobic fermentation for one week at 37° C.;

⑥ Fermentation with *Clostridium butyricum:* 1-1.5% of lactose is added into the fermentation broth, and *Clostridium butyricum* (ATCC 19398) is inoculated, followed by anaerobic fermentation for one week at 37° C.;

The enzyme solution fermented under an anaerobic condition is oxygenated for 1-2 h every two days, and the oxygen supply to the enzyme solution fermented under aerobic and facultative anaerobic conditions is stopped for 2-3 h every two days. Meanwhile, the temperature-varied exercise of ±2-4° C. is carried out every day, thereby improving the stress resistance of the bacterial flora, and improving the strength of the probiotics. The appropriate low pressure is kept in the entire fermentation process, and the pressure is returned after the fermentation broth is disturbed for 0.5-1 h by introducing the nitrogen every day, so that the sediments are re-suspended, and the fermentation efficiency can be improved.

(5) Precise Intensification and Mixing of Probiotics

The concentrated probiotics are precisely intensified and mixed for different target groups. The saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth are mixed in a ratio of 1:1:1:1:1:1 for general population, in a ratio of 1:2:2:2:2:1 for people having intestinal microecological disorders caused by antibiotics, in a ratio of 1:1:2:1:2:1 for people having intestinal microecological disorders caused by high-fat diet, in a ratio of 1:1:2:1:2:1 for people having the intestinal microecological disorders caused by the psychological stress and physical stress and in a ratio of 1:2:2:1:2:2 for people having the intestinal microecological disorders caused by advanced ages.

(6) Filtration

By virtue of three-level filtration, suspended solids and undecomposed residues on the surface are removed.

(7) Flavoring Agent is Added, Followed by Blending and Stirring 3-4 wt % of sucrose, 1-3 wt % of honey, 1-2 wt % of brown sugar, and 1-1.5 wt % of dark brown sugar are added and fully and uniformly stirred.

(8) Chelating and Aging in a Dark Place

The blended apple enzymes are sealed, and stand at a dark place for chelating and aging for 1 to more than six months. The apple enzymes are aged for one month to obtain the low-quality and medium-quality apple enzymes, and aged for more than six months to obtain high-quality apple enzymes.

(9) Regular Air Exhaustion

A cover is opened for air exhaustion every 15 days during the later aging period.

(10) Filtration

The filtration is carried out again before a finished product is obtained to remove the suspended solids and undecomposed residues on the surface as well as dead valueless probiotics flora and excrement deposited on the bottom.

TABLE 1

Detection of patulin residue

| Method | Apple raw stock | Detoxification with plant lactobacillus | Adsorption with carboxylation nano multi wall carbon and aluminum oxide | Combined detoxification |
|---|---|---|---|---|
| Detected amount of residues | >75-90 µg/kg | 4.6-5.7 µg/kg | 24-33 µg/kg | 0.9-1.5 µg/kg |

Note:
the health standard for the limited quantity of patulin in China is not greater than 50 µg/kg.

TABLE 2

Contrast of effective components (content of the component in every 100 g of enzymes

| Main component | Common enzymes | Antibiotic disorder treatment type | High-fat obesity treatment type | Psychological stress and physical stress treatment type | Advanced-age people healthcare type |
|---|---|---|---|---|---|
| Energy (KJ) | 313 | 307 | 177 | 334 | 297 |
| Fat (g) | 2.3 | 2.2 | 0.5 | 2.2 | 2.1 |
| Carbohydrate (g) | 13.7 | 14.1 | 5.9 | 19.9 | 11.4 |
| Proteins (g) | 0.6 | 1.1 | 0.9 | 3.3 | 2.9 |
| Dietary fibers (g) | 1.2 | 0.7 | 2.9 | 1.1 | 1.1 |
| Vitamin C (mg) | 3.7 | 4.4 | 4.2 | 4.8 | 4.3 |
| Vitamin E (mg) | 0.19 | 0.19 | 0.15 | 0.29 | 0.19 |
| Vitamin D (mg) | 0 | 0 | 0.3 | 0.44 | 0.23 |
| Vitamin B (mg) | 0.05 | 3.3 | 1.7 | 0.03 | 1.8 |
| Calcium Ca (mg) | 3.3 | 3.4 | 2.9 | 5.5 | 5.4 |
| Folic acid (microgram) | 3.5 | 3.9 | 3.5 | 3.1 | 3.3 |
| Pantothenic acid (microgram) | 0.03 | 0.05 | 0.03 | 0.04 | 0.97 |

What is claimed is:

1. A processing method of an apple enzyme for reconstruction of an intestinal microecology, comprising the following steps:

(1) pretreating raw materials, comprising:

removing molded parts of post-floral fallen fruits and young fruits, washing ash and soil on the surfaces of the fruits, reserving wild yeasts of pericarp, removing cores and dicing;

(2) pulping with low-temperature liquid nitrogen-reducing browning of pulp compared to untreated pulp; controlling the low temperature at 5-10° C., wherein a dripping amount of the liquid nitrogen is 2%-3.5%; after the pulping, carrying out an enzymolysis by reducing a pressure, adding 50 mg/L-70 mg/L of pectinase and 85 mg/L-100 mg/L of cellulase, and stirring for 1-2 h at 40-45° C.;

(3) detoxifying patulin, comprising:

firstly biologically detoxifying the pulp, comprising: inoculating *Lactobacillus plantarum* (ATCC 8014) into the pulp, adjusting the pH to 3-7 at the temperature of 20-30° C., stirring, and detoxifying for 20-24 h; and then repeatedly absorbing and filtering with a carboxylated nano multiwall carbon-neutral aluminum oxide filter screen for three times;

(4) carrying out a dynamic fermentation, comprising:

adding an agent into the detoxified apple pulp, wherein the agent is composed of trehalose, mannitol and cysteine in a weight ratio of (1-2):(1-1.5):(1-2); and then equally dividing the apple pulp into six portions for separate fermentation, fermenting with Saccharomycetes, *Lactobacillus plantarum, Lactobacillus acidophilus*, probiotic *Bacillus, Bifidobacterium* and *Clostridium butyricum;* supplying oxygen to the enzyme solution fermented under an anaerobic condition for 1-2 hours every two days, and stopping the oxygen supply to the enzyme solution fermented under aerobic and facultative anaerobic conditions for 2-3 hours every two days; at the same time, carrying out a fluctuate temperature exercise at a rate of ±2-4° C. every day; and maintaining an appropriate pressure in the entire fermentation process, introducing the nitrogen to disturb a fermentation broth for 0.5-1 h every day, then returning the pressure, and re-suspending sediments;

① fermenting with Saccharomycetes, comprising: adding fruit *Saccharomyces cerevisiae* (ATCC 9080) into the fermentation broth, and fermenting for 12 days at 28-30° C.;
② fermenting with *Lactobacillus plantarum*, comprising: adding 1%-1.5% of albumen powder into the fermentation broth, and inoculating *Lactobacillus plantarum* (ATCC 8014), followed by anaerobic fermentation for one week at 36-40° C.;
③ fermenting with *Lactobacillus acidophilus*, comprising: adding 2-3% of lactose and 1-1.5% of fructo-oligose into the fermentation broth, and inoculating *Lactobacillus acidophilus* (AS 1.1854), followed by oxygen-free fermentation for one week at 37° C.;
④ fermenting with probiotic *Bacillus*, comprising: adding 1%-1.5% of albumen powder and 2-2.5% of starch into the fermentation broth, and inoculating probiotic *Bacillus* (CGMCC1.3358), followed by aerobic fermentation for one week at 37° C.;

⑤ fermenting with *Bifidobacterium*, comprising: adding 2-3% of oligosaccharide and 1-1.5% of fructo-oligose into the fermentation broth, and inoculating *Bifidobacterium* (ATCC 15700), followed by the anaerobic fermentation for one week at 37° C.; and ⑥ fermenting with *Clostridium butyricum*, comprising: adding 1-1.5% of lactose into the fermentation broth, and inoculating *Clostridium butyricum* (ATCC 19398), followed by the anaerobic fermentation for one week at 37° C.;

(5) mixing the probiotics, comprising: mixing six fermentation broths in the above steps for use;

(6) carrying out three-level filtration to remove suspended solids and undecomposed residues on a surface;

(7) adding a flavoring agent, blending and stirring, comprising:

adding 3-4 wt % of sucrose, 1-3 wt % of honey, 1-2 wt % of brown sugar, and 1-1.5 wt % of dark brown sugar, and stirring;

(8) chelating and aging in a dark place, comprising:

sealing the blended apple enzymes, standing in a dark place, chelating and aging for 1 to more than 6 months, aging for one month to obtain the low-quality and medium-quality apple enzymes, and aging for more than six months to obtain the high-quality apple enzymes;

(9) exhausting air regularly, comprising: opening a cover for air exhaustion every 15 days during a later aging period; and

(10) filtering again before obtaining the finished product.

2. The processing method of the apple enzyme for reconstruction of the intestinal microecology of claim 1, wherein a method for mixing the probiotics in step (5) comprises the following steps:

mixing the saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth in a ratio of 1:1:1:1:1:1 for general population;

mixing the saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth in a ratio of 1:1:1:1:1:1 for general population in a ratio of 1:2:2:2:2:1 for people having intestinal microecological disorders caused by antibiotics;

mixing the saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth in a ratio of 1:1:1:1:1:1 for general population in a ratio of 1:1:2:1:2:1 for people having intestinal microecological disorders caused by high-fat diet;

mixing the saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth in a ratio of 1:1:1:1:1:1 for general population in a ratio of 1:1:2:1:2:1 for people having the intestinal microecological disorders caused by a psychological stress and physical stress; and mixing the saccharomycetes fermentation broth, the *Lactobacillus plantarum* fermentation broth, the *Lactobacillus acidophilus* fermentation broth, the probiotic *bacillus* fermentation broth, the *Bifidobacterium* fermentation broth and the *Clostridium butyricum* fermentation broth in a ratio of 1:1:1:1:1:1 for general population in a ratio of 1:2:2:1:2:2 for people having the intestinal microecological disorders caused by advanced ages.

3. The processing method of the apple enzyme for reconstruction of the intestinal microecology of claim 1, wherein a structure of the carboxylated nano multiwall carbon-neutral aluminum oxide filter screen is that the filter screen has a five-layer structure, wherein a first layer is a sieve plate with an aperture of 5-10 meshes and a diameter of 2-4 mm; a second layer is carboxylation nano multiwall carbon with a particle size of 3-5 nm; a third layer is macroporous adsorption resin; a fourth layer is neutral aluminum oxide with a particle size of 50-70 μm; a fifth layer is also a sieve plate with an aperture of 5-10 meshes; and a pulp containing solute with a particle size not greater than 3 mm can pass through an adsorption filter screen.

* * * * *